US010584091B2

(12) United States Patent
Campbell et al.

(10) Patent No.: US 10,584,091 B2
(45) Date of Patent: Mar. 10, 2020

(54) PROCESS FOR THE RECOVERY OF DIALKYL SUCCINATE OR DIALKYL MALEATE

(71) Applicant: JOHNSON MATTHEY DAVY TECHNOLOGIES LIMITED, London (GB)

(72) Inventors: Ian Campbell, London (GB); Stephen Carrett, London (GB); Michael William Marshall Tuck, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 165 days.

(21) Appl. No.: 15/569,946

(22) PCT Filed: Mar. 23, 2016

(86) PCT No.: PCT/GB2016/050829
§ 371 (c)(1),
(2) Date: Oct. 27, 2017

(87) PCT Pub. No.: WO2016/174388
PCT Pub. Date: Nov. 3, 2016

(65) Prior Publication Data
US 2019/0152889 A1    May 23, 2019

(30) Foreign Application Priority Data

Apr. 28, 2015   (GB) .................................. 1507234.1

(51) Int. Cl.
*C07C 67/58* (2006.01)
*C07C 67/54* (2006.01)
*C07C 67/08* (2006.01)
*C07C 29/147* (2006.01)

(52) U.S. Cl.
CPC ............ *C07C 67/58* (2013.01); *C07C 29/147* (2013.01); *C07C 67/08* (2013.01); *C07C 67/54* (2013.01)

(58) Field of Classification Search
CPC ......... C07C 67/08; C07C 69/40; C07C 67/54; C07C 69/60; C07C 67/58; C07C 29/147
See application file for complete search history.

(56) References Cited

U.S. PATENT DOCUMENTS

| 2,766,273 | A | * | 10/1956 | Canapary | ................. | C07C 69/67 |
|  |  |  |  |  |  | 530/232 |
| 4,032,458 | A | * | 6/1977 | Cooley | ................. | C07C 29/177 |
|  |  |  |  |  |  | 560/190 |
| 4,584,419 | A |  | 4/1986 | Sharif et al. |  |  |
| 4,656,297 | A |  | 4/1987 | Kouba et al. |  |  |
| 4,751,334 | A |  | 6/1988 | Turner et al. |  |  |
| 4,767,869 | A |  | 8/1988 | Harrison et al. |  |  |
| 4,795,824 | A |  | 1/1989 | Kippax et al. |  |  |
| 4,919,765 | A |  | 4/1990 | Wilkes et al. |  |  |
| 4,945,173 | A |  | 7/1990 | Wood |  |  |
| 5,157,168 | A |  | 10/1992 | Wilmott et al. |  |  |
| 5,254,758 | A |  | 10/1993 | Hiles et al. |  |  |
| 5,310,954 | A |  | 5/1994 | Hiles et al. |  |  |
| 5,536,856 | A | * | 7/1996 | Harrison | ................. | B01D 3/163 |
|  |  |  |  |  |  | 261/108 |
| 5,958,744 | A |  | 9/1999 | Berglund et al. |  |  |
| 6,265,190 | B1 |  | 7/2001 | Yedur et al. |  |  |
| 8,246,792 | B2 |  | 8/2012 | Fruchey et al. |  |  |

FOREIGN PATENT DOCUMENTS

| CN | 101343210 A |  | 1/2009 |
| CN | 01343211 A |  | 10/2013 |
| CN | 103360206 A |  | 10/2013 |
| WO | WO1986003189 |  | 11/1985 |
| WO | WO8800937 A1 |  | 2/1988 |
| WO | WO1988000937 |  | 2/1988 |
| WO | WO1990008127 |  | 7/1990 |
| WO | WO1991001960 |  | 2/1991 |
| WO | WO1999035113 |  | 7/1999 |
| WO | WO1999035136 |  | 7/1999 |
| WO | WO2013/188162 | * | 12/2013 |
| WO | WO2015082915 A1 |  | 6/2015 |
| WO | WO2015082916 A1 |  | 6/2015 |

OTHER PUBLICATIONS

GB 1507234.1, Search Report Under Section 17(5) dated Feb. 4, 2016.
PCT/GB2016/050829, International Search Report dated Jun. 1, 2016.
PCT/GB2016/050829, Written Opinion dated Jun. 1, 2016.

* cited by examiner

*Primary Examiner* — Yevgeny Valenrod
*Assistant Examiner* — Blaine G Doletski
(74) *Attorney, Agent, or Firm* — BakerHostetler

(57) ABSTRACT

A process for recovering product dialkyl succinate, dialkyl maleate or dialkyl succinate and dialkyl maleate from an overhead stream from an esterification reaction column, said overhead stream comprising as a major component alkanol and water and as a minor component the product dialkyl succinate, dialkyl maleate or dialkyl succinate and dialkyl maleate which forms an azeotrope with the water, wherein said process comprises washing the overhead stream with butanol.

13 Claims, 5 Drawing Sheets

PROCESS FOR THE RECOVERY OF DIALKYL SUCCINATE OR DIALKYL MALEATE

CROSS-REFERENCE TO RELATED APPLICATIONS

This application is the National Stage of International Patent Application No. PCT/GB2016/050829 filed Mar. 23, 2016, which claims priority from Great Britain Patent Application No. 1507234.1 filed Apr. 28, 2015, the disclosures of each of which are incorporated herein by reference in their entirety.

The present invention relates to a process for the recovery of dialkyl succinate or dialkyl maleate from a stream recovered as overhead from an esterification reaction column. More particularly, the present invention relates to a process for the recovery of dimethyl succinate or dimethyl maleate recovered as overhead from an esterification reaction column.

It is known to produce diols by reaction of dicarboxylic acids and/or anhydrides, or mono- or di-alkyl esters, lactones, or mixtures thereof with hydrogen. Commercially, where the desired product is 1,4-butanediol, typically with the co-products tetrahydrofuran and γ-butyrolactone, the starting material is normally a dialkyl ester of maleic acid and/or anhydride, such as dimethyl maleate or diethyl maleate, which may contain minor amounts of dialkyl fumarate and/or dialkyl succinate.

Information relating to these processes can be found in, for example, U.S. Pat. Nos. 4,584,419, 4,751,334, WO86/03189, WO88/00937, U.S. Pat. Nos. 4,767,869, 4,945,173, 4,919,765, 5,254,758, 5,310,954 and WO91/01960.

The dialkyl maleates which are used as feedstock in these conventional reaction processes may be produced by any suitable means. The production of dialkyl maleates for use in such processes is discussed in detail in U.S. Pat. Nos. 4,584,419, 4,751,334, WO88/00937, U.S. Pat. No. 4,795,824 and WO90/08127.

In one conventional process for the production of 1,4-butanediol and co-product tetrahydrofuran with optional production of γ-butyrolactone, a dialkyl ester, such as dimethyl maleate together with any residual methanol from the esterification reactor, is fed to a vaporiser where it is vaporised by a stream of hot cycle gas fed to the vaporiser which may be mixed with make-up hydrogen. The cycle gas will normally contain a high concentration of hydrogen gas but may also include other gases including hydrocarbons, carbon oxides, methane and nitrogen. Further, where the cycle gas includes recycled gases from downstream, condensables including product ether, methanol, water, co-products and by-products may also be present.

The combined vaporous stream from the vaporiser is then passed to a reactor where it is reacted in the presence of a catalyst to form 1,4-butanediol, tetrahydrofuran and/or γ-butyrolactone. The product stream is cooled and the reaction products are condensed and separated from the excess cycle gas before being passed into a refining zone. In the refining zone the various products are separated and the 1,4-butanediol and the tetrahydrofuran are removed. The γ-butyrolactone, together with the intermediate, dimethyl succinate, and some 1,4-butanediol may be recycled. In one arrangement the γ-butyrolactone may be at least partially extracted in an optional refining zone and recovered. The methanol water stream separated from the product mix will be recycled upstream. In general, a significant portion of the 1,4-butanediol produced by this or other conventional methods is subsequently converted to tetrahydrofuran.

The overall reaction which occurs is a series of steps and may include a final dehydration step in which tetrahydrofuran is produced. A probable reaction path starting from the dimethyl maleate is set out in Scheme 1.

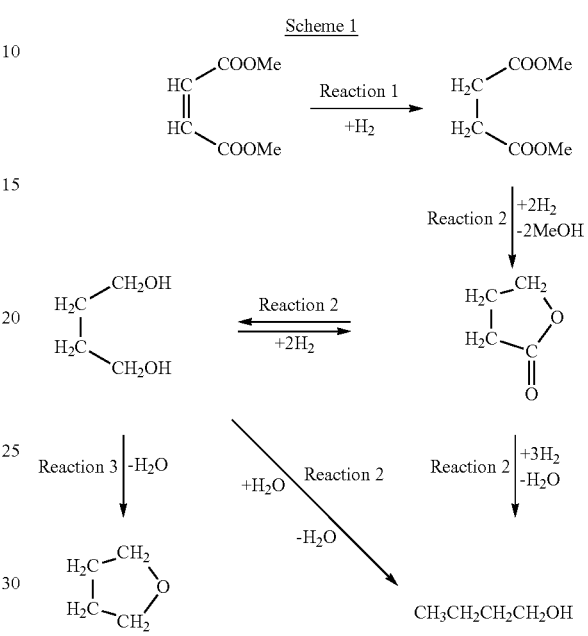

An alternative process is described in WO99/35113 in which maleic anhydride esters are fed to a reaction process in which three different catalysts are used. First the maleate is converted to the succinate in the presence of the first catalyst which is a heterogeneous selective hydrogenation catalyst at a temperature of from 120° C. to 170° C. and a pressure of 3 to 40 bara. The succinate is then passed directly to the presence of the second catalyst where it is converted mainly into γ-butyrolactone. The product of the reaction with the second catalyst is then fed directly to the presence of a third catalyst which is used to dehydrate the γ-butyrolactone to produce tetrahydrofuran. Some of the γ-butyrolactone formed in the presence of the second catalyst is transferred to a second reaction loop operating at a higher pressure where it is converted to 1,4-butanediol.

As the first step in Scheme 1 and the first catalyst used in the alternative process described in WO99/35113 relates to the hydrogenation of the dimethyl maleate to dimethyl succinate, it has been suggested that dimethyl succinate or diethyl succinate may be suitable starting materials for the reaction with hydrogen to form 1,4-butanediol, tetrahydrofuran and/or γ-butyrolactone.

One process in which dimethyl succinate is used in the production of tetrahydrofuran and 1,4-butanediol is described in U.S. Pat. No. 4,656,297. In this process, methanol is added to the ester feed to increase conversion and reduce transesterification. Another example of a process in which dimethyl succinate is suggested as a feed is WO99/35136 in which reaction with hydrogen occurs over two different catalysts, to form a mixture of tetrahydrofuran and γ-butyrolactone.

Recently, there have been significant advancements in processes to produce and recover succinic acid from the fermentation of sugars. Examples of such processes can be found in, for example, U.S. Pat. Nos. 5,958,744, 6,265,190 and 8,246,792. Currently demonstration plants have been constructed. It is anticipated that in due course such processes may be able to compete with maleic anhydride as an economic feedstock for the production of 1,4-butanediol.

For ease of reference, succinic acid produced from biological sources optionally by fermentation processes will be referred to as 'bio-succinic acid' and the term should be construed accordingly. Any suitable fermentation process may be used. As bio-succinic acid generally contains impurities such as fermentation residues and by-products, whilst bio-succinic acid can be used in conventional processes designed for succinic acid, particular advantages can be observed where processes are specifically tailored to handle these impurities. An example of one suitable process is that described in WO2015/082916. In this process the reaction is a counter-current reaction. An alternative arrangement is described in WO2015/082915 in which co-current reaction occurs.

Whether the starting material is maleic acid, maleic anhydride, succinic acid (including bio-succinic acid), or succinic anhydride, or monoalkyl esters thereof, the first step in the production of the 1,4-butanediol, tetrahydrofuran and/or γ-butyrolactone is the formation of the dialkyl ester. There are many processes known for the production of the dialkyl ester but conventionally the reaction is carried out in a reaction column in which the acid or anhydride is fed to a reaction column where it flows downwardly against an upward flow of alcohol. As the acid passes down the column it contacts progressively drier alcohol which assists to drive the equilibrium of the reaction towards completion.

Although esterification reactions can be autocatalysed, a catalyst will generally be used, particularly where a di-alkyl ester is to be formed. The catalyst will generally be located on trays within the reaction column. In some cases, particularly where a dialkyl ester such as dialkyl succinate is to be formed, a pre-reaction to the monoalkyl ester will be carried out, and it is the monoalkyl ester which is fed to the reaction column. However, although the pre-reaction is primarily for the formation of the monoalkyl ester, it will be understood that some dialkyl ester will be formed.

As reaction progresses in the reaction column, the product dialkyl ester will be removed from at, or near, the bottom of the reaction column and the alcohol, which is used to an excess, together with the water formed during the reaction will be removed from the reaction column at or near the top. This stream will be referred to as the 'overhead stream'.

However, whilst the ester will generally be removed from at, or near, the bottom of the column, some ester is lost into the aqueous overhead stream. This is particularly problematic where there has been pre-reaction since this will mean some dialkyl ester will be introduced toward the upper portion of the reaction column close to the portion of the column from where the overhead stream is removed.

Whilst these problems may arise with the production of dialkyl maleate in a reaction column starting with maleic anhydride, it is particularly problematic where the feed to the reaction column is succinic acid where there will generally be a pre-reaction to form the monoalkyl ester before reaction to form the dialkyl ester commences. Where an anhydride such as maleic anhydride is used as the starting material, the loss can be controlled by limiting the amount of alcohol such that the mono-ester is preferentially formed as no water is released. In contrast, where a di-acid is used as the starting material as the mono-ester is formed, water is released. Since esterification of the acid is a reversible reaction, conversion is limited. Thus to achieve the same conversion for an acid starting material when compared to the anhydride starting material a greater stoichiometric excess of alcohol will need to be added. This means that unreacted acid, mono-ester and di-ester will all be present.

In this connection, it is observed that losses of dimethyl succinate formed from succinic acid in the overhead stream are higher than those observed in the corresponding system for the production of dimethyl maleate which is generally formed from maleic anhydride.

One reason for this is that the dialkyl succinate is more volatile that the equivalent dialkyl maleate. Further, as discussed above, there is more likely to be a pre-reaction process where the starting material is succinic acid and thus the feed to the top of the reaction column will contain a higher proportion of the dialkyl ester when compared to the flowsheet in which maleic acid or anhydride is the starting material where pre-reaction is more uncommon.

Where the alcohol used in the production of the dialkyl ester of succinic acid is methanol, dimethyl succinate will be formed. Dimethyl succinate forms a low boiling azeotrope with water at approximately 2 mol % dimethyl succinate at a temperature just below the boiling point of pure water. Thus where the dimethyl succinate is carried over in the aqueous overhead stream, it can be difficult to recover using conventional distillation or phase separation techniques. In this connection, it is noted that the azeotrope composition appears to lie outside, or at the very limit of, the immiscible region when cooled to near ambient temperature which makes phase separation inefficient.

Whether the dialkyl ester is dialkyl succinate or dialkyl maleate, the failure to recover any dialkyl ester carried over in the overhead stream results in a loss to the reaction which has a substantial negative impact on the overall process economics.

A further problem is that the presence of the dialkyl ester in the overhead stream will mean that the aqueous effluent stream will have a high organic loading. Indeed, the loading may be as high as about 5 wt % where the ester is dialkyl succinate. This loading will increase the cost of treating the effluent stream before it can be released to the environment.

Further, the dialkyl ester present in the overhead stream may be hydrolysed back to the monoalkyl ester or the starting acid during any future treatment of the overhead stream. For example, where there is an alkanol column for separating the alkanol from water, the hydrolysis of any ester present in the overhead stream may occur in the bottom of the alkanol column due to the high water and low alkanol content which creates equilibrium conditions favouring the reverse reaction.

Where hydrolysis does take place, significant concentrations of monoalkyl ester, dicarboxylic acid or both monoalkyl ester and dicarboxylic acid may build up in the bottom of the alkanol column. Where this occurs, the risk of corrosion and fouling is increased.

The problems detailed above will occur with the production of any dialkyl maleate in a reaction column but they are particularly problematic where the dialkyl ester of succinic acid is being formed, particularly where dimethyl succinate is being formed.

Some proposals have been made relating to recovering ester carried in the overhead stream. In U.S. Pat. No. 5,536,856 a process for forming an ester is discussed. Whilst there is a suggestion that an alkanol wash may be used to remove ester from the overhead stream, there is no suggestion as to how removal can be affected where the ester forms a low boiling azeotrope with water.

Methanol is suggested as being useful as a wash to recover traces of fatty ester or acid in overheads in U.S. Pat. No. 5,157,168. However, again there is no suggestion as to how removal can be affected where the ester forms a low boiling azeotrope with water.

It is therefore desirable to provide a process which provides a low boiling azeotrope with water which is more volatile than, for example, the water/dimethyl succinate azeotrope and therefore provides for the removal of dialkyl succinate or maleate from an overhead stream from a reaction column in which the dialkyl succinate or maleate is formed.

It has now been found that the dialkyl succinate or maleate carried in the overhead stream can be recovered therefrom by washing the overhead stream with butanol which will enable the dialkyl succinate or maleate to be separated from the overhead stream. To minimise costs, the butanol with which the overhead stream is contacted may be obtained from within the overall flowsheet.

Thus according to the present invention, there is provided a process for recovering product dialkyl succinate, dialkyl maleate, or dialkyl succinate and dialkyl maleate from an overhead stream from an esterification reaction column, said overhead stream comprising as a major component alkanol and water and as a minor component the product dialkyl succinate, dialkyl maleate or dialkyl succinate and dialkyl maleate which forms an azeotrope with the water, wherein said process comprises washing the overhead stream with butanol.

The wash with butanol enables the product dialkyl succinate or maleate to be separated from the major component of the overhead stream. Since the wash stream will enable the product dialkyl succinate or maleate to be separated from the major component of the overhead stream, it can be recovered and therefore the presence of product dialkyl succinate or maleate in the overhead stream from the reaction column does not represent a loss of product to the system.

The overhead stream may be subjected to washing as a first step as it is removed from the reaction column or it may be subjected to processing before being subjected to washing.

In one arrangement, the butanol for use in the present invention may be recovered from within the flowsheet as this will be more cost-effective than supplying a separate stream. In this connection, it will be understood that the flowsheet may include post-esterification reaction steps. Thus, for example, since dialkly succinate or dialkyl maleate are often used in the production of 1,4-butanediol, tetrahydrofuran, or γ-butyrolactone, the butanol for use as the wash stream may be that recovered from the hydrogenation process in the manufacture of 1,4 butanediol, tetrahydrofuran, or γ-butyrolactone which occurs after the esterification reaction. This offers particular advantages as the product butanol is normally purged and therefore use is made of a stream which would generally be lost and no new components have to be added which could cause further side chemistry.

Whilst butanol is the wash stream of the present invention, it will be understood that other alkanols may be used. For example, alkanols having from two to four carbon atoms may be used.

The wash may be carried out at any suitable place in the flowsheet. In one arrangement, the overhead recovered from the reaction column may be passed to a flash column where it is washed with the butanol. In this arrangement, the product dialkyl succinate or maleate will be recovered from the bottom of the flash column. It can then be passed to a suitable place in the flowsheet. In one arrangement, it is returned to the reaction column in which esterification occurs. The overhead from the flash column will be water, the excess alkanol from the esterification and butanol which can then be passed to an alkanol column for separation.

Where the overhead from the flash column is passed to an alkanol column rather than being recycled, butanol and water may be removed from the alkanol column as a side draw. This side draw may be cooled. Although butanol does form an azeotrope with the water, the azeotrope composition lies within the immiscible region when the liquid is cooled so that the butanol and water will separate. The butanol may be recovered and used to provide reflux to the flash column while the aqueous phase may be recycled to the alkanol column.

Heat exchangers may be present to allow heat integration between various streams in the flowsheet.

Where the ester is dimethyl succinate and butanol is used as a wash in a flash column, over 90% of the dimethyl succinate losses associated with the original flowsheet are recovered and can be returned to the reactor.

A further advantage of this arrangement of the present invention is that the conventional wash with the alkanol used for esterification at the top of reduction will generally no longer be required. This will reduce the overall height of the column when compared with conventional reaction columns thereby reducing capital and operating goods.

In addition, where the requirement for the conventional wash is removed, the alkanol which would conventionally be used for this purpose no longer has to be processed through the alkanol column before it can be used in the esterification reaction which will therefore reduce the energy requirements for the reboiler of the alkanol column.

A reboiler will generally be required on the flash column to force water overhead and to pre-heat the feed to the reaction column.

The flash column may be integrated with the reaction column. In this arrangement, the column will include discrete reaction and rectifying sections. This may therefore mean that the present invention may be retrofitted into a reaction column with a conventional methanol wash whereby the butanol wash is used in place of the methanol wash.

In one arrangement, the alkarlol column may be split into two. In this arrangement, the bottom liquid from the upper section of the alkanol column may be fed to a decanter in which the butanol is separated from the aqueous component. The aqueous component would then be fed to the top of the lower section of the alkanol column. The vapour overhead from the lower section of the alkanol column is fed to the bottom of the upper section. This allows flexibility of reflux ratios, draw rates and the like. It may also allow a lower grade of steam to be used to reboil the upper section of the column since its composition would give it a lower bubble point for the same pressure.

Whilst the process of the present invention may be used with dialkyl maleate, it offers particular advantages when operated where the feed to the esterification reaction is succinic anhydride, succinic acid, mono succinic acid esters or mixtures thereof. These may be co-fed to the reaction column or they may be fed separately to the reaction column.

The dialkyl succinate or maleate may be dimethyl or diethyl succinate or maleate, with the dimethyl ester being particularly preferred.

According to a second aspect of the present invention there is provided a process for the manufacture of 1,4- butanediol with optional co-products tetrahydrofuran and and/or γ-butyrolactone and by-product butanol comprising;

forming dialkyl succinate, dialkyl maleate or dialkyl succinate and dialkyl maleate in a reaction column;

removing the dialkyl succinate, dialkyl maleate or dialkyl succinate and dialkyl maleate from at or near the reaction column bottom and further treating the ester to form 1,4-butanediol with optional co-products tetrahydrofuran and and/or γ-butyrolactone and by-product butanol;

recovering dialkyl succinate, dialkyl maleate or dialkyl succinate and dialkyl maleate from an overhead stream from the reaction column in accordance with the above first aspect wherein the butanol used to wash the overhead stream is by-product butanol.

The present invention will now be described, by way of example, by reference to the accompanying drawings in which.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The process of the present invention will be discussed with reference to the recovery of dimethyl succinate which is used in the production of 1,4-butanediol. However, it is equally applicable to the recovery of other dialkyl esters including dialkyl maleate.

Figure 1:
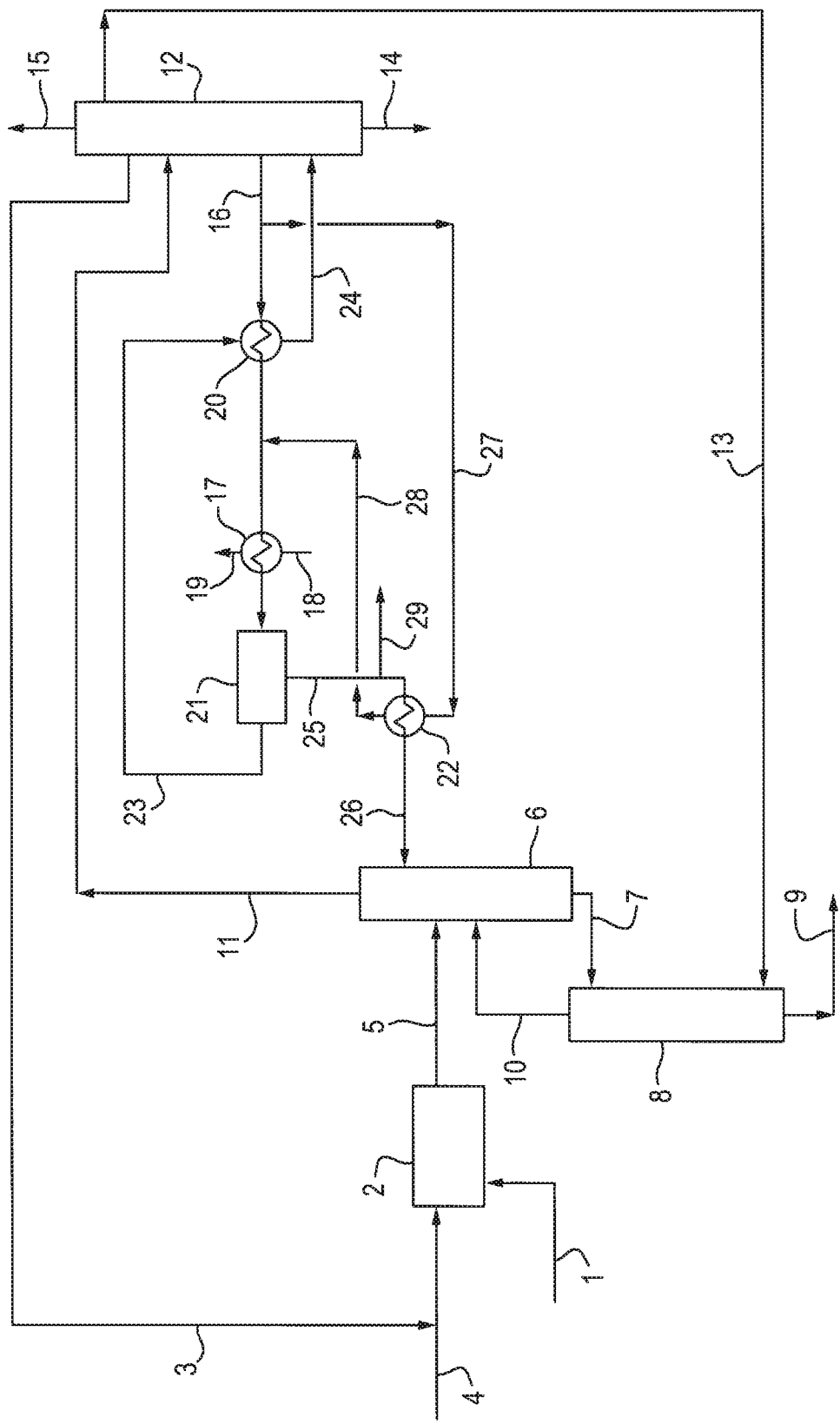
FIG. 1 is a schematic representation of a process in accordance with a first aspect of the present invention.

A schematic illustration of the process of one embodiment of the present invention is illustrated in FIG. 1. In this embodiment the succinic acid is fed in line 1 to a pre-reactor 2 where it is contacted with methanol. The methanol may be recycled methanol returned from methanol column 12 and/ or fresh or make up methanol added in line 4. In the pre-reactor some esterification may occur.

The stream from the pre-reactor 2 is passed in line 5 to the flash column 6 and then in line 7 to the esterification reactor 8 where further esterification occurs. A side boiler, not shown, will generally be found towards the bottoms of the flash column 6.

The product dimethyl succinate is removed in column bottom 9 and will then be passed to hydrogenation for the reaction to 1,4-butanediol.

The overhead stream from the reaction column 8, which will contain, as a main component, water and methanol and, as a minor component, dimethyl succinate, is recovered in line 10 and passed to flash column 6.

A butanol wash stream is fed to the flash column 6 in line 26. In practice it will be about 60 to 70 wt % butanol. The butanol will remove the dimethyl succinate from the water and methanol. The dimethyl succinate will then be returned to the reaction column 8 in line 7.

Water and butanol form a low boiling azeotrope at approximately 26 mol % butanol at an operating pressure of the flash column of about 1.6 bara. It will be understood that other operating pressures may be used.

The butanol wash is used to approach the water/butanol azeotrope composition toward the top of the flash column 6, and generally in the top tray of the flash column 6, and prevent dimethyl succinate from concentrating and leaving in the overhead from the flash column.

At a temperature of 102.6° C. and a pressure of 1.6 bara, the water/butanol azeotrope is more volatile than the water/ dimethyl succinate azeotrope at 111.7° C., which significantly, by over 90%, reduces the concentration of the dimethyl succinate in the column overheads.

The overhead from the flash column which will comprise water, methanol and butanol will be passed in line 11, optionally through a partial condenser (not shown), to the methanol column 12 where separation occurs. This stream may comprise about 25 wt % water. The partial condenser will generally be used if the flash column is operated at elevated temperatures. The separated methanol is removed in overhead stream 15 and may be recycled to the esterification reactor or to any pre-reactor. The separated water is removed from the column bottom in line 14.

Methanol may be removed from towards the top of the methanol column 12 and recycled to the esterification reactor 8 in line 13 to provide the methanol for the esterification. This stream will preferably have a purity of about 99.95%. A stream 3 may be removed from the methanol column 12 at a point below where the pure methanol stream is removed. Although this methanol stream will have a lower purity that the methanol recovered in line 13, it will be suitable for supplying to the pre-reactor.

Butanol will be removed from the methanol column 12 in side draw 16. The butanol stream recovered from the methanol column 12 will be cooled, generally to about 40° C. such that some phase separation may occur. This may be carried out in heat exchanger 17 against cooling water supplied in line 18. This will then be recycled for re-use via line 19.

However, in an alternative arrangement, two additional heat exchangers may be included in the loop to improve heat integration. The first heat exchanger 20 interchanges the hot water-butanol draw with the cooled aqueous phase exiting the decanter 21 thus reheating the stream returned to the methanol column 12 and thereby reducing the reboiler duty for the methanol column.

The second additional heat exchanger 22 interchanges the hot water-butanol draw against the cooled organic phase exiting the decanter 21, thereby reheating the stream before it is supplied as reflux in line 26 to the flash column 6 thereby reducing the flash column reboiler duty.

Thus in this arrangement, the butanol/water side draw is removed from the methanol column 12 in line 16 and passed to heat exchanger 20 where it is cooled against an aqueous stream recovered from the decanter 21. It is then further cooled against cooling water in heat exchanger 17 before being passed to decanter 21. The aqueous stream is recovered in line 23 which is passed in counter-current heat exchange in exchanger 20 before being passed in line 24 back to the methanol column 12.

The organic phase from the decanter 21 is removed in line 25. It is then passed through heat exchanger 22 before being fed to the flash column 6. The hot stream against which the organic phase from the decanter in line 25 is heated is taken from the side draw 16 in line 27. This cooled stream is passed back to the stream to the heat exchanger 17 in line 28. A purge may be removed in line 29.

Any suitable conditions may be used for the butanol wash. In one arrangement, the flash column may be operated at an overheads pressure of about 1.6 bara, a flash column reflux ratio of 0.1 to 0.2. The recovery of dimethyl succinate in the flash column bottom stream will be about 97%. The water/butanol draw rate from the methanol column as a percentage of liquid traffic in the column will be about 40 to about 100% with the optimum being around 50%.

Where an autocatalytic esterification reaction is carried out the flash column and the reaction column may be operated at a pressure of about 7.8 bara. This may require an increased reflux ratio of 0.3 to 0.4 for the flash column to achieve comparable recovery of the dimethyl succinate. The increased pressure will allow some useful heat to be recovered from the overhead stream from the flash column by condensing the stream before it is passed to the methanol column 12.

Where a butanol wash is supplied to the flash column, the amount of dimethyl succinate lost and the heat input required are controlled by two main variables, namely the reflux ratio in the flash column and the water-butanol draw rate from the methanol column. These two variables are interlinked and for a given flash column reflux ratio, there is a minimum draw rate required in order to satisfy it.

Figure 2:
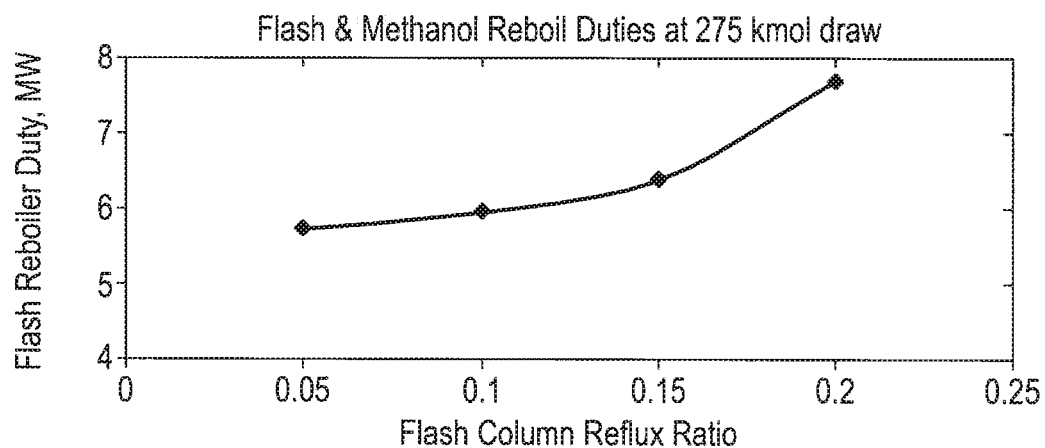
FIG. 2 is a graph illustrating the flash and methanol column reboil duties in the first aspect of the present invention.
Figure 3:
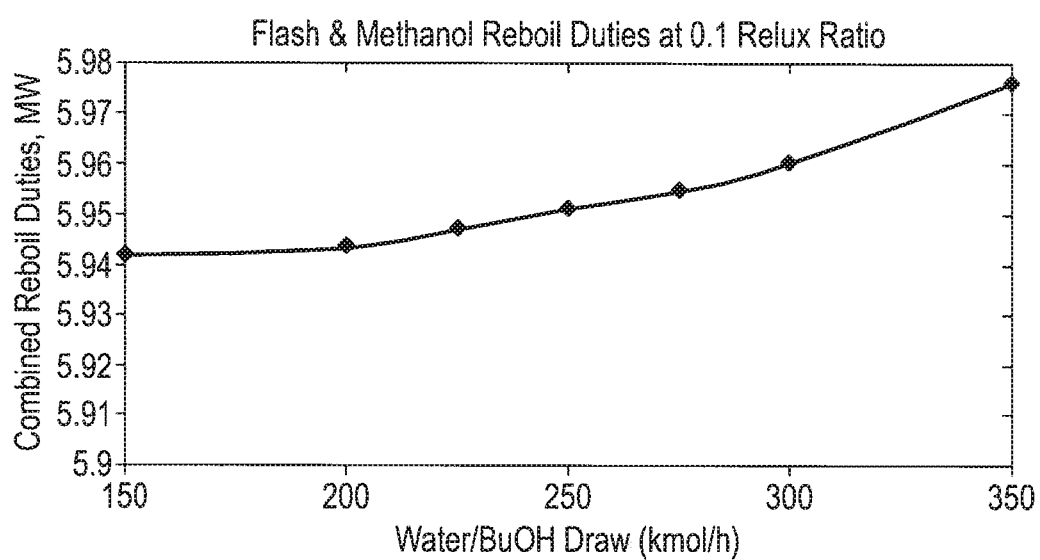
FIG. 3 is a graph illustrating reboil duties at 0.1 reflux ratio in the first aspect of the present invention.

As illustrated in FIG. 2, the heat input required to the flash column and methanol column reboilers increases appreciably with the reflux ratio in the flash column. However, as illustrated in FIG. 3, the heat input is largely insensitive to the water/butanol draw rate.

Figure 4:
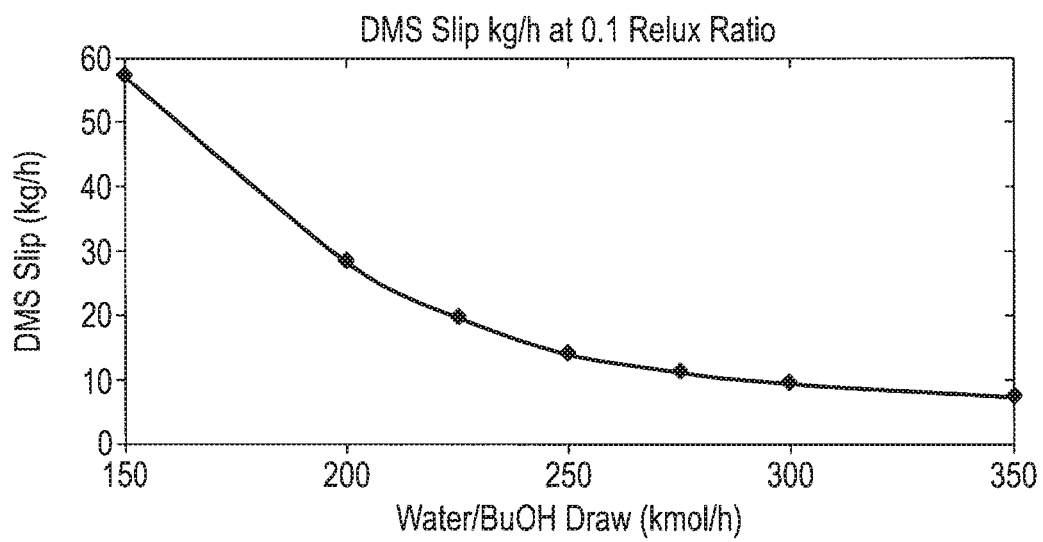
FIG. 4 is a graph illustrating dimethyl succinate slip at a 0.1 reflux ratio in the reboil duties in the first aspect of the present invention.
Figure 5:
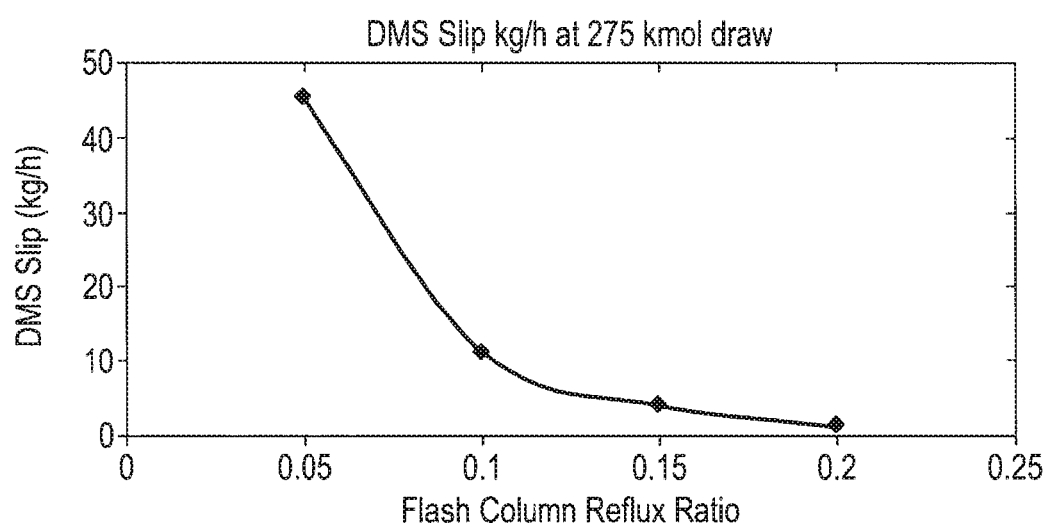
FIG. 5 is a graph illustrating dimethyl succinate slip at 275 kmol draw.

As can be seen from FIGS. 4 and 5, the dimethyl succinate slip is strongly influenced by the flash column reflux ratio, and is also influenced by the draw rate from the methanol column.

Increasing the draw rate from the methanol column to the decanter increases the amount of butanol in circulation and can thus increase the concentration of butanol in the flash column, allowing the flash column overheads composition to more closely approach the water/butanol azeotrope, which improves the exclusion of dimethyl succinate from the flash column overheads.

Figure 6:
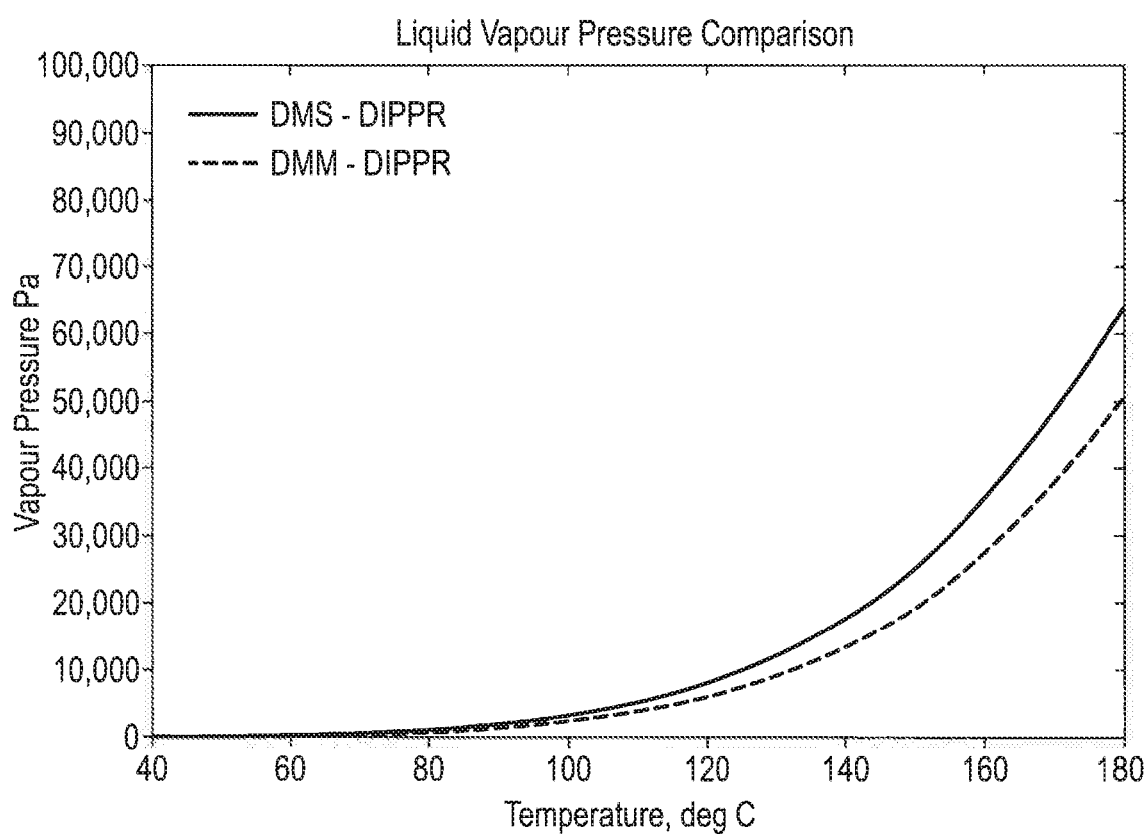
FIG. 6 is a graph comparing the liquid vapour pressure of dimethyl succinate and dimethyl maleate.

A comparison between the liquid vapour pressures of dimethyl maleate and dimethyl succinate is illustrated in FIG. 6. The differences in the liquid vapour pressure will result in more dimethyl succinate being carried in the overhead stream from the reaction column than will be noted for dimethyl maleate. Whilst the butanol wash may also be used to recover dimethyl maleate carried in column overhead from the reaction to produce dimethyl maleate, the small amount carried over may not make the economics of using the process of the present invention viable.

The present invention will now be further described with reference to the following examples:

Comparative Example 1

All testwork was performed using an oil jacketed continuous stirred tank reactor unit fitted with 500 mL reaction flask. Stirring was via an overhead Teflon stirrer at 300 rpm. An air condenser, heated to a controlled temperature by a laboratory heating tape, was added to the overheads off take at an angle of approximately 25° from vertical. The resulting overheads stream was condensed using a standard Leibig water cooled condenser.

300 g of petrochemical monomethyl succinate feed (86% acid) with a small amount of dimethyl succinate and unreacted succinic anhydride present was fed to the reaction vessel. The feed was heated to 115° C. prior to adding 30 g (methanol washed and dried) of DPT-2 resin to the vessel. DPT-2 is a catalyst available from Johnson Matthey Davy Process Technologies Limited.

Once at the desired temperature and after the addition of the DPT-2 resin, methanol was introduced continuously at a rate of 218.2 gh$^{-1}$ (3 molar equivalence to monomethyl succinate) using a peristaltic pump via a submerged dip leg. Regular samples of the overhead stream and the pot contents were taken. The lights, dimethyl succinate, water and methanol were collected as a condensable liquid overhead that was weighed on sampling. The pot contents were sampled in order for the monomethyl succinate concentration to be determined by titration against 0.1 M KOH using ethanolic phenolphthalein as the indicator.

The overheads were analysed by gas chromatography. The water content in the overheads stream was determined by Karl Fisher volumetric analysis. This allowed the actual mass of dimethyl succinate lost in the overheads stream to be determined with time and hence the rate of dimethyl succinate loss per hour was calculated. The results are set out in Table 1.

TABLE 1

| Time min | Pot Temp ° C. | Methanol Rate g h-1 | Pot Acidity wt % | Overheads Collected g | Water in Overheads wt % | Dimethyl Succinate in Overheads wt % | Dimethyl Succinate Lost g | Cumulative Dimethyl Succinate Loss g |
|---|---|---|---|---|---|---|---|---|
| 0 | 111 | 261 | 88.99 | — | — | — | — | — |
| 15 | 113 | 218 | 51.52 | 38.0 | 26.2 | 9.09 | 3.5 | 3.5 |
| 30 | 115 | 218 | 31.2 | 61.8 | 22.62 | 14.37 | 8.9 | 12.4 |
| 60 | 115 | 213 | 6.16 | 119.4 | 9.2 | 15.85 | 18.9 | 31.3 |
| 120 | 115 | 213 | 0.42 | 249.1 | 0.67 | 17.07 | 42.5 | 73.8 |
| 180 | 115 | 213 | 0.22 | 248.4 | 0.24 | 17.19 | 42.7 | 116.5 |
| 220 | 115 | 213 | 0.31 | 162.7 | 0.21 | 17.39 | 28.3 | 144.8 |

Example 2

Comparative Example 1 was repeated with butanol (18 vol % h$^{-1}$ vs methanol mL h$^{-1}$) being fed continuously to the top of the air condenser using a peristaltic pump. The results are set out in Table 2.

TABLE 2

| Time min | Pot Temp °C. | Methanol Rate g h-1 | Pot Acidity wt % | Overheads Collected g | Water in Overheads wt % | Dimethyl Succinate in Overheads wt % | Dimethyl Succinate Lost g | Cumulative Dimethyl Succinate Loss g |
|---|---|---|---|---|---|---|---|---|
| 0 | 112 | 217 | 69.6 | — | — | — | — | — |
| 15 | 114 | 213 | 45.35 | 37.5 | 21.94 | 4.68 | 1.8 | 1.8 |
| 30 | 115 | 212 | 23.28 | 67.0 | 22.24 | 6.14 | 4.1 | 5.9 |
| 45 | 115 | 219 | 10.09 | 68.9 | 13.78 | 6.73 | 4.6 | 10.5 |
| 60 | 115 | 218 | 3.95 | 69.1 | 6.74 | 7.01 | 4.8 | 15.3 |
| 90 | 115 | 219 | 0.57 | 138.2 | 1.60 | 7.34 | 10.1 | 25.4 |
| 120 | 115 | 194 | 0.32 | 134.7 | 0.47 | 6.76 | 9.1 | 34.5 |
| 180 | 115 | 194 | 0.34 | 249.2 | 0.31 | 6.35 | 15.8 | 50.3 |

Figure 7:
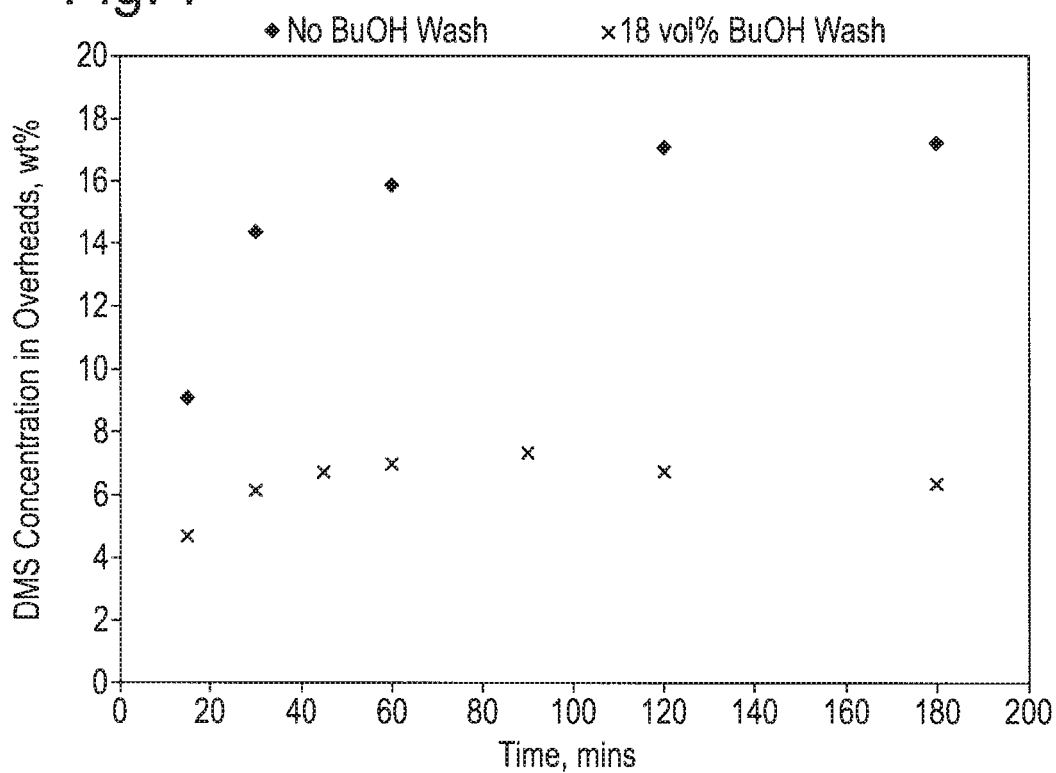
FIG. 7 is a graph comparing dimethyl succinate concentration in the overhead stream according to Comparative Example 1 and Example 2.
Figure 8:
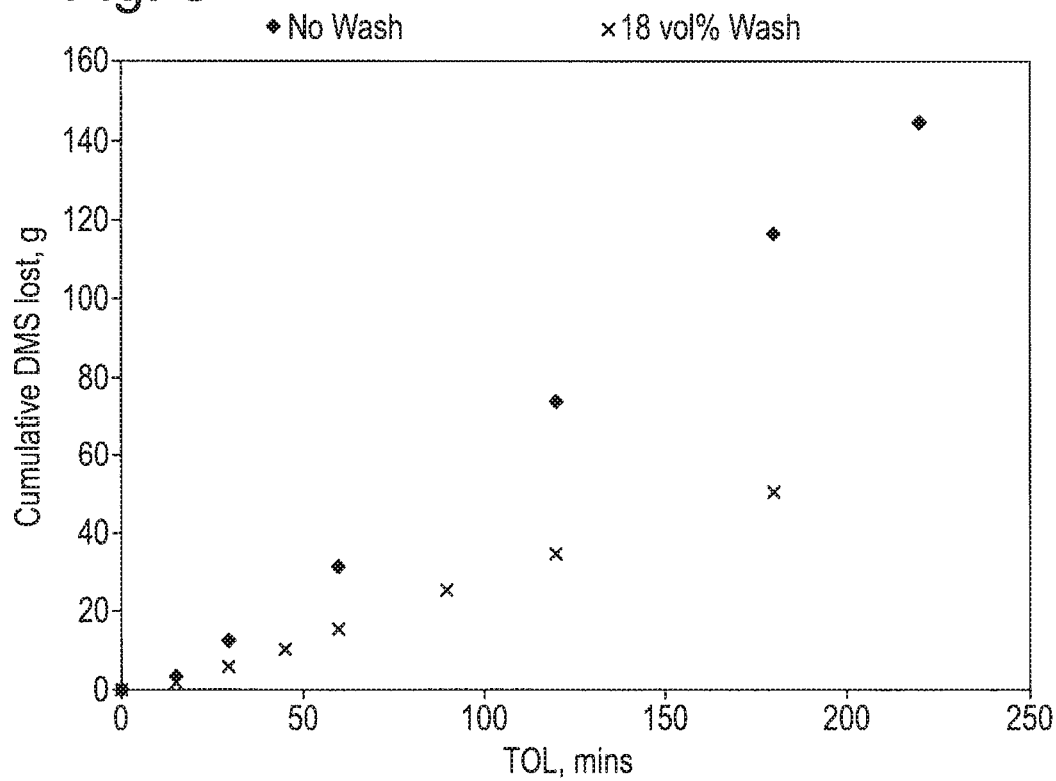
FIG. 8 is a graph comparing the cumulative loss of dimethyl succinate according to Comparative Example 1 and Example 2.

The change in concentration of dimethyl succinate in the overhead stream over time and the cumulative loss of dimethyl succinate over time is illustrated in FIGS. 7 and 8 respectively.

These figures demonstrate the positive effect of the butanol wash. In particular, it can be seen that the concentration of dimethyl succinate in the overhead stream was significantly lower when the wash was used. Further, the mass of dimethyl succinate lost was significantly less when the wash was used.

The invention claimed is:

1. A process for recovering product dimethyl or diethyl succinate, dimethyl or diethyl maleate, or dimethyl or diethyl succinate and dimethyl or diethyl maleate from an overhead stream from an esterification reaction column, said overhead stream comprising as a major component alkanol and water and as a minor component the product dimethyl or diethyl succinate, dimethyl or diethyl maleate, or dimethyl or diethyl succinate and dimethyl or diethyl maleate which forms an azeotrope with the water, wherein said process comprises washing the overhead stream with butanol.

2. The process according to claim 1, wherein the butanol wash stream is a stream recovered from within the flowsheet.

3. The process according to claim 1, wherein the overhead stream is contacted with butanol in a flash column.

4. The process according to claim 3, wherein the overhead stream from the reaction column is passed to a flash column without prior separation.

5. The process according to claim 1, wherein the dimethyl or diethyl succinate, dimethyl or diethyl maleate, or dimethyl or diethyl succinate and dimethyl or diethyl maleate recovered from the overhead stream in the flash column is returned to the reaction column.

6. The process according to claim 3, wherein the overhead stream from the flash column is passed to an alkanol column for further separation.

7. The process according to claim 6, wherein butanol and an aqueous phase is removed from the alkanol column in a side draw.

8. The process according to claim 7, wherein the side draw is cooled before being passed to a decanter.

9. The process according to claim 8, wherein the butanol separated in the decanter is returned to the flash column.

10. The process according to claim 9, wherein the butanol is heated against a stream recovered from an alkanol column before it is returned to the flash column.

11. The process according to claim 8, wherein the aqueous stream from the decanter is returned to the alkanol column.

12. The process according to claim 11, wherein the aqueous phase is heated against the side draw from the alkanol column before it is returned to the alkanol column.

13. A process for the manufacture of 1,4-butanediol with optional co-products tetrahydrofuran and/or γ-butyrolactone and by-product butanol comprising;

forming dimethyl or diethyl succinate, dimethyl or diethyl maleate, or dimethyl or diethyl succinate and dimethyl or diethyl maleate in a reaction column;

removing the dimethyl or diethyl succinate, dimethyl or diethyl maleate, or dimethyl or diethyl succinate and dimethyl or diethyl maleate from at or near the reaction column bottom and further treating the ester to form 1,4-butanediol with optional co-products tetrahydrofuran and/or γ-butyrolactone and by-product butanol;

recovering dimethyl or diethyl succinate, dimethyl or diethyl maleate, or dimethyl or diethyl succinate and dimethyl or diethyl maleate from an overhead stream from the reaction column in accordance with claim 1, wherein the butanol used to wash the overhead stream is by-product butanol.

* * * * *